United States Patent
Perronnet et al.

[11] 3,948,925
[45] Apr. 6, 1976

[54] NOVEL THIAZOLE DERIVATIVES

[75] Inventors: Jacques Perronnet, Paris; Laurent Taliani, Les Pavillons-sous-Bois, both of France

[73] Assignee: Roussel-UCLAF, Paris, France

[22] Filed: Oct. 17, 1974

[21] Appl. No.: 515,479

[30] Foreign Application Priority Data
Oct. 25, 1973 France .............................. 73.38071

[52] U.S. Cl. ... 260/302 E; 260/302 R; 260/306.7 R; 424/200
[51] Int. Cl.² ...................................... C07D 277/34
[58] Field of Search ............................... 260/302 E

[56] References Cited
UNITED STATES PATENTS

| | | | |
|---|---|---|---|
| 3,159,645 | 12/1964 | Rigterink | 260/302 E |
| 3,687,963 | 8/1972 | Hoffmann et al. | 260/302 E |
| 3,758,487 | 9/1973 | Hoffmann et al. | 260/302 E |
| 3,784,554 | 1/1974 | Barker | 260/302 E |

OTHER PUBLICATIONS
Bayer, Chem. abstracts, 62:9139, (1965).

*Primary Examiner*—R. J. Gallagher
*Attorney, Agent, or Firm*—Hammond & Littell

[57] ABSTRACT
Novel compounds of the formula

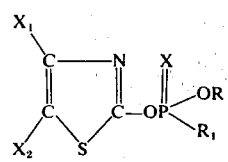

wherein X is selected from the group consisting of oxygen and sulfur, $X_1$ is selected from the group consisting of alkyl of 1 to 6 carbon atoms, cyano and

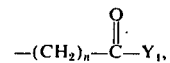

$Y_1$ is selected from the group consisting of alkyl of 1 to 6 carbon atoms, alkoxy of 1 to 6 carbon atoms and amino, n is 0, 1 or 2, $X_2$ is selected from the group consisting of hydrogen, chlorine, bromine, alkyl of 1 to 6 carbon atoms, cyano and

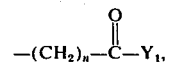

R is alkyl of 1 to 6 carbon atoms, $R_1$ is selected from the group consisting of alkyl of 1 to 6 carbon atoms, alkoxy of 1 to 6 carbon atoms and

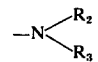

and $R_2$ and $R_3$ are selected from the group consisting of hydrogen and alkyl of 1 to 6 carbon atoms with the proviso that $X_1$ is other than alkyl when $X_2$ is alkyl or hydrogen, having insecticidal, nematocidal and acaricidal properties.

23 Claims, No Drawings

NOVEL THIAZOLE DERIVATIVES

STATE OF THE ART

French Patent No. 1,384,282 describes thiazoline derivatives slightly different from the compounds of formula I and their use for the protection of plants and to combat ecto- and endoparasites in warm-blooded animals.

OBJECTS OF THE INVENTION

It is an object of the invention to provide the novel thiazoline compounds of formula I and to provide a novel process for their preparation.

It is a further object of the invention to provide novel insecticidal compositions and to provide a novel method of combatting insects.

These and other objects and advantages of the invention will become obvious from the following detailed description.

THE INVENTION

The novel thiazolines of the invention have the formula

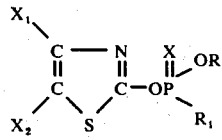

wherein X is selected from the group consisting of oxygen and sulfur, $X_1$ is selected from the group consisting of alkyl of 1 to 6 carbon atoms, cyano and

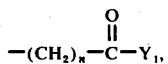

$Y_1$ is selected from the group consisting of alkyl of 1 to 6 carbon atoms, alkoxy of 1 to 6 carbon atoms and amino, $n$ is 0, 1 or 2, $X_2$ is selected from the group consisting of hydrogen, chlorine, bromine, alkyl of 1 to 6 carbon atoms, cyano and

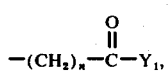

R is alkyl of 1 to 6 carbon atoms, $R_1$ is selected from the group consisting of alkyl of 1 to 6 carbon atoms, alkoxy of 1 to 6 carbon atoms and

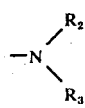

and $R_2$ and $R_3$ are selected from the group consisting of hydrogen and alkyl of 1 to 6 carbon atoms with the proviso that $X_1$ is other than alkyl when $X_2$ is alkyl or hydrogen.

Among the preferred compounds of formula I are those where X is sulfur, $X_1$ is alkyl of 1 to 6 carbon atoms, cyano or

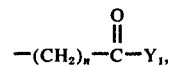

$Y_1$ is alkyl or alkoxy of 1 to 3 carbon atoms or amino, $n$ is 0, 1 or 2, $X_2$ is hydrogen, bromine, chlorine, or identical to $X_1$, R is defined as above and $R_1$ is alkoxy of 1 to 3 carbon atoms, methyl or methylamino. Two preferred compounds are 4-isopropoxycarbonyl-2-(diethoxythiophosphoryloxy)-thiazole and 4-ethoxycarbonylmethyl-2-(diethoxythiophosphoryloxy)-thiazole.

The novel process of the invention for the preparation of the compounds of formula I comprises reacting in the presence of a basic agent a thiazole of the formula

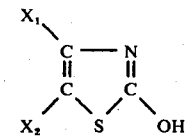

with a compound of the formula

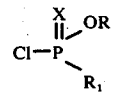

wherein $X_1$, $X_2$, X, R and $R_1$ have the above definitions. The basic agent is preferably an alkali metal carbonate, an alkali metal alcoholate or a tertiary amine. The condensation reaction is preferably effected in an organic solvent such as acetone or tetrahydrofuran.

Some of the products of formula II are known and some are novel but most of Them may be prepared by reacting ethyl thiocarbamate with a compound of the formula

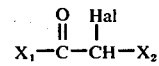

5-cyano-4-methyl-4-thiazoline-2-one may be prepared by condensing 3-amino-crotononitrile and chlorocarbonylsulfenyl chloride and 5-bromo-4-ethoxycarbonyl-4-thiazoline-2-one may be prepared by reacting 4-ethoxycarbonyl-4-thiazoline-2-one and bromine. 4-carbamoyl-4-thiazoline-2-one may be prepared by reacting ammonium hydroxide and 4-methoxycarbonyl-4-thiazoline-2-one.

The novel compositions of the invention are comprised of an effective amount of at least one compound of formula I and a carrier. The compositions possess insecticidal, nematocidal and acaricidal activity and are useful in the agricultural field.

Tests have shown the compositions to be effective against insects such as Spodoptera exigua caterpillars, Chilo suppressalis caterpillars, Sitophilus granarius, drosophila melanogaster, Blatella germanica and Mamestra oleracea caterpillars. The acaricidal properties have been demonstrated on Tetranychus Urticae and the nematocidal activity has been shown on Panagrellus silusae, Ditylenchus myceliophagus and meloidogynes.

The compositions may be in the form of suspensions, solutions or emulsions containing the active products, for example in admixture with a vehicle and/or an anionic, cationic or non-ionic surface active agent to ansure a uniform dispersion of the substances of the composition among other reasons. The vehicle may be, for example, water, an alcohol, a hydrocarbon or other organic solvent or a mineral, animal or vegetable oil.

The insecticidal liquid compositions for foliar spraying preferably contain 10 to 80% by weight of the active product and acaricidal liquid compositions for foliar spraying preferably contain 20 to 80% by weight of the active product. The nematocidal liquid compositions for soil treatment preferably contain 40 to 95% by weight of the active product.

An example of an insecticidal composition of the invention is an emulsifiable concentrate comprised of 15% by weight of 4-ethoxycarbonyl-2-(diethoxythiophosphoryloxy)-thiazole, 6.4% by weight of Atlox 4851 [oxyethylene triglyceride combined with a sulfonate with an acid number of 1.5[, 3.2% by weight of Atlox 4855 [oxyethylene triglyceride combined with a sulfonate with an acid number of 3] and 75.4% by weight of xylene In the following examples there are described several preferred embodiments to illustrate the invention. However, it should be understood that the invention is not intended to be limited to the specific embodiments.

EXAMPLE 1

5-ethoxycarbonyl-4-methyl-4-thiazoline-2-one 84 g of ethyl thiocarbamate were added to 500 ml of dioxane and then 168 g of ethyl α-bromoacetylacetate was added thereto dropwise. The mixture was refluxed for 4 hours and the solvent was then evaporated under reduced pressure. The solid residue was crystallized from benzene to obtain 72g of 5-ethoxycarbonyl-4-methyl-4-thiazoline-2-one in the form of white crystals melting at 172°C.

Analysis: $C_7H_9NO_3S$ Calculated: %C 44.9, %H 4.8, %N 7.5 %S 17.1; Found: %C 44.9, %H 4.9, %N 7.7, %S 17.2.

Usng the above procedures, the halogenated compound listed in Table I was reacted to obtain the corresponding 4-thiazoline-2-one of Table I.

EXAMPLE 2

5-acetyl-2-(diethoxythiophosphoryloxy)-4-methylthiazole

A mixture of 7.8 g of 5-acetyl-4-methyl-4-thiazoline-2-one and 10.5 g of potassium carbonate in 400 ml of acetone was refluxed for 1 hour and after the addition of 14.1 g of 0,0-diethyl chlorothiophosphate, the mixture was refluxed for 1 hour. The mixture was filtered to remove mineral salts and the filtrate was distilled to dryness under reduced pressure. The residue was chromatographed over silica gel and was eluted with an 8-2 cyclohexane-ethyl acetate mixture to obtain 6.5 g of 5-acetyl-2-(diethoxythiophosphoryloxy)-4-methylthiazole with a refractive index of $n_D^{22} = 1.5288$ Analysis: $C_{10}H_{16}NO_4PS_2$ Calculated: %C 38.83, %H 5.21, %N 4.53 %P 10.01; Found: %C 39.0, %H 5.1, %N 4.2, %P 10.0.

EXAMPLE 3

5-bromo-4-ethoxycarbonyl-2-(diethoxythiophosphoryloxy)-thiazole

STEP A: 5-bromo-4-ethoxycarbonyl-4-thiazoline-2-one 69 g of bromine were added to a mixture of 69.2 g of 4-ethoxycarbonyl-4-thiazoline-2-one in 500 ml of chloroform and the mixture was refluxed for 20 hours. The mixture was distilled to dryness under reduced pressure and after the addition of isopropyl ether, the mixture was vacuum filtered to obtain 75.2 g of 5-bromo-4-ethoxycarbonyl-4-thiazoline-2-one melting at 121°C.

Analysis: $C_6H_6BrNO_3S$ Calculated: %C 28.59, %H 2.40, %N 5.56, %Br 31.69, %S 12.71; Found: %C 29.2, %H 2.4, %N 5.4, %Br 31.4, %S 12.6.

STEP B: 5-bromo-4-ethoxycarbonyl-2-(diethoxythiophosphoryloxy)-thiazole 9.4 g of 0,0-diethyl chlorothiophosphate were added to a mixture of 12.6 g of 5-bromo-4-ethoxycarbonyl-4-thiazoline-2-one and 5 g of triethylamine in 300 ml of tetrahydrofuran and the mixture was stirred for 20 hours at room temperature and filtered. The filtrate was evaporated to dryness under reduced pressure and the residue was chromatographed over silica gel. Elution with an 8-2 cyclohexane-ethylacetate mixture gave 6.2 g of 5-bromo-4-ethoxycarbonyl-2-(diethoxythiophosphoryloxy)-thiazole with a refractive index of $n_D^{22} = 1.5356$.

Analysis: $C_{10}H_{15}BrNO_5PS_2$
Calculated: %C 29.71, %H 3.74, %N 3.47, %Br 19.77, %P 7.67; Found: %C 29.8, %H 3.7, %N 3.5, %Br 19.9, %P 7.5.

TABLE I

| Starting halide | Product of formula II | Melting point °C |
| --- | --- | --- |
| $BrCH_2COCOOCH_3$ | 4-methoxycarbonyl 4-thiazoline 2-one | 143 |
| $BrCH_2COCOOC_2H_5$ | 4-ethoxycarbonyl 4-thiazoline 2-one | 108 |
| $BrCH_2COCOOCH(CH_3)_2$ | 4-isopropyloxycarbonyl 4-thiazoline 2-one | 115 |
| $CH_3COCOCH_2Br$ | 4-acetyl 4-thiazoline 2-one | 216 |
| $CH_3COCHClCOCH_3$ | 5-acetyl 4-methyl 4-thiazoline 2-one | 216 |
| $BrCH_2COCH_2COOC_2H_5$ | 4-ethoxycarbonylmethyl 4-thiazoline 2-one | 107 |
| $CH_3OCOCHClCOCH_2COOCH_3$ | 5-methoxycarbonyl 4-methoxycarbonylmethyl 4-thiazoline 2-one | 92 |
| $C_2H_5OCOCHClCOCOOC_2H_5$ | 4,5-di-ethoxycarbonyl 4-thiazoline 2-one | 68 |
| $C_2H_5OCOCH_2CHBrCOCOOC_2H_5$ | 4-ethoxycarbonyl 5-ethoxycarbonylmethyl 4-thiazoline 2-one | 78 |
| $C_2H_5OCOCH_2COCHBrCH_2COOC_2H_5$ | 4,5-di-ethoxycarbonylmethyl 4-thiazoline 2-one | oil |
| $CH_3(CH_2)_5CHClCOCOOC_2H_5$ | 4-ethoxycarbonyl 5-n-hexyl 4-thiazoline 2-one | oil |

EXAMPLE 4

4-acetyl-2-(diethoxythiophosphoryloxy)-thiazole

A mixture of 14.3 g of 4-acetyl-4-thiazoline-2-one and 13.8 g of potassium carbonate in 400 ml of acetone was refluxed for one hour and after the addition of 18.8 g of 0,0-diethyl chlorothiophosphate, the mixture was refluxed for another hour. The mixture was then stirred for 48 hours at room temperature and was filtered to remove mineral salts. The filtrate was evaporated to drynss under reduced pressure and the residue was chromatographed over silica gel. Elution with an 8-2 cyclohexane-ethylacetate mixture resulted in 9.2 g of 4-acetyl-2-(diethoxythiophosphoryloxy)-thiazole with a refractive index of $n_D^{21} = 1.5258$.

Analysis: $C_9H_{14}NO_4PS_2$ Calculated: %C 36.62, %H 4.78, %N 4.77, %P 10.48, %S 21.72; Found: %C 37.4, %H 4.8, %N 4.6, %P 10.5, %S 21.5.

EXAMPLE 5

5-ethoxycarbonyl-2-(diethoxythiophosphoryloxy)-4-methyl-thiazole

A mixture of 12.8 g of sodium methylate and 32.5 g of 5-ethoxycarbonyl-4-methyl-4-thiazoline-2-one in 1 liter of methanol was stirred for 1 hour at room temperature and the solvent was distilled off under reduced pressure. 500 ml of acetone were added to the residue and after the addition of 38 g of 0,0-diethyl chlorothiophosphate, the mixture was stirred for 48 hours at room temperature. The mixture was filtered to remove sodium chloride and the filtrate was distilled to dryness under reduced pressure. The residue was chromatographed over silica gel and elution was effected with a 9-1 cyclohexane-ethyl acetate mixture to obtain 23.8 g of 5-ethoxycarbonyl-2-(diethoxythiophosphoryloxy)-4-methyl-thiazole with a refractive index of $n_D^{20} = 1.507$ Analysis: $C_{11}H_{18}NO_5PS_2$ Calculated: %C 38.9, %H 5.4, %N 4.1, %P 9.1; Found: %C 38.9, %H 5.5, %N 4.0, %P 9.3.

EXAMPLE 6

4-cyano-2-(diethoxythiophosphoryloxy)-thiazole

A mixture of 176 g of β-bromopyruvaldoxime [J. Org. Chem., Vol. 38 (1973), p. 807] and 70 g of ethyl thiocarbamate in 500 ml of dioxane was refluxed for 18 hours and the dioxane was then evaporated. The resulting solid product effloresced upon the addition of isopropyl ether and the resulting crystals were recovered by vacuum filtration which was used as is for the next step.

4.3 g of the said crystals were then mixed with 8.4 g of potassium carbonate in 200 ml of acetone and the mixture was refluxed for 2 hours. 11.4 g of 0,0-diethyl chlorothiophosphate were added thereto and the mixture was refluxed for 16 hours and then was cooled. The mixture was filtered and the filtrate was evaporated to dryness. The residue was chromatographed over silica gel and elution with an 8-2 cyclohexane-ethylacetate mixture gave 1 g of 4-cyano-2-(diethoxythiophosphoryloxy)-thiazole in the form of a colorless oil.

Analysis: $C_8H_{11}N_2O_3PS_2$ Calculated: %C 34.52, %H 3.99, %N 10.07, %P 11.1; Found: %C 34.5, %H 4.1, %N 10.4, %P 10.8.

EXAMPLE 7

5-cyano-4-methyl-4-thiazoline-2-one 40 g of chlorocarbonylsulfenyl chloride were added to a mixture of 25 g of 3-amino-crotononitrile in 700 ml of tetrahydrofuran and the mixture was refluxed for 3 hours after which the solvent was distilled off under reduced pressure. The residue was heated at 140°C for 10 minutes and cooled and then 1N sodium hydroxide was added thereto. The aqueous solution was washed with ethylacetate, acidified with hydrochloric and extracted with ethylacetate. The organic extracts were dried, concentrated to dryness and isopropyl ether was added to obtain 31 g of 5-cyano-4-methyl-4-thiazoline-2-one melting at 180° to 181°C.

Analysis: $C_5H_4N_2OS$ Calculated: %C 42.85, %H 2.88, %N 19.99 %S 22.88; Found: %C 42.9, %H 2.6, %N 19.9, %S 22.8.

EXAMPLE 8

4-aminocarbonyl-4-thiazoline-2-one 48 g of 4-methoxycarbonyl-4-thiazoline-2-one were added to 600 ml of concentrated aqueous ammonium hydroxide and the mixture was stirred for 24 hours. The mixture was acidified and filtered to obtain 30 g of 4-aminocarbonyl-4-thiazoline-2-one in the form of white crystals melting at 261°C.

Analysis: $C_4H_4N_2O_2S$ Calculated %C 33.32, %H 2.79, %N 19.43, %S 22.25; Found: %C 33.4, %H 2.7, %N 19.1, %S 22.1.

EXAMPLE 9

Using the procedure of Example 6, the appropriate thiazoline-2-ones were reacted to obtain the corresponding thiazole of Table II.

TABLE II

| Starting Material | Product of Formula I | Refractive index or melting point |
|---|---|---|
| 5-methoxycarbonyl-4-methoxycarbonylmethyl-4-thiazoline-2-one | 5-methoxycarbonyl-4-methoxycarbonylmethyl-2-(diethoxythiophosphoryloxy)-thiazole | $n_D^{16} = 1.5138$ |
| 5-ethoxycarbonylmethyl-4-methyl-4-thiazoline-2-one | 5-ethoxycarbonylmethyl-2-(diethoxythiophosphoryloxy)-4-methyl-thiazole | $n_D^{22} = 1.506$ |
| 5-cyano-4-methyl-4-thiazoline-2-one | 5-cyano-2-(diethoxythiophosphoryloxy)-4-methyl-thiazole | $n_D^{20} = 1.530$ |
| 4-ethoxycarbonyl-4-thiazoline-2-one | 4-ethoxycarbonyl-2-(diethoxythiophosphoryloxy)-thiazole | $n_D^{20} = 1.5178$ |
| 4,5-diethoxycarbonyl-4-thiazoline-2-one | 4,5-diethoxycarbonyl-2-(diethoxythiophosphoryloxy)-thiazole | $n_D^{20} = 1.5076$ |
| 4-ethoxycarbonyl-5-n-hexyl-4-thiazoline-2-one | 4-ethoxycarbonyl-2-(diethoxythiophosphoryloxy)-5-n-hexyl-thiazole | $n_D^{20} = 1.5041$ |
| 4-ethoxycarbonyl-5-ethoxycarbonylmethyl-4-thiazoline-2-one | 4-ethoxycarbonyl-2-(diethoxythiophosphoryloxy)-5-ethoxycarbonylmethyl-thiazole | $n_D^{21} = 1.5078$ |
| 4-methoxycarbonyl-4-thiazoline- | 4-methoxycarbonyl-2-(diethoxythio- | $n_D^{21} = 1.5202$ |

TABLE II-continued

| Starting Material | Product of Formula I | Refractive index or melting point |
|---|---|---|
| 2-one | phosphoryloxy)-thiazole | |
| 4-isopropoxycarbonyl-4-thiazoline-2-one | 4-isopropoxycarbonyl-2-(diethoxythiophosphoryloxy)-thiazole | $n_D^{19} = 1.5082$ |
| 4-ethoxycarbonylmethyl-4-thiazoline-2-one | 4-ethoxycarbonylmethyl-2-(diethoxythiophosphoryloxy)-thiazole | $n_D^{21} = 1.508$ |
| 4-carbamoyl-4-thiazoline-2-one | 4-carbamoyl-2-(diethoxythiophosphoryloxy)-thiazole | $F = 46°C$ |
| 4,5-di-(ethoxycarbonylmethyl)-4-thiazoline-2-one | 4,5-di-(ethoxycarbonylmethyl)-2-(diethoxythiophosphoryloxy)-thiazole | $n_D^{21} = 1.4988$ |
| 5-ethoxycarbonyl-4-[(2'-ethoxycarbonyl)-ethyl]-4-thiazoline-2-one | 5-ethoxycarbonyl-4-[(2'-ethoxycarbonyl)-ethyl]-2-(diethoxythiophosphoryloxy)-thiazole | $n_D^{21} = 1.5050$ |
| 4-ethoxycarbonyl-4-thiazoline-2-one | N-methyl-thiophosphoramidate of O-ethyl and O-[2-(4-ethoxycarbonyl-thiazolyle)] | $n_D^{19} = 1.5288$ |
| 4-ethoxycarbonyl-4-thiazoline-2-one | methylthiophosphonate of O-ethyl and O-[2-(4-ethoxycarbonylthiazolyle)] | $n_D^{23} = 1.5346$ |

EXAMPLE 10

2-(diethoxythiophosphoryloxy)-4-(2'-butoxycarbonyl)-thiazole

A mixture of 29 g of 4-carboxy-4-thiazoline-2-one [Enlenmeyer et al, Helv., Chim. Acta., Vol. 27 (1944), p.1432-6] and 200 ml of thionyl chloride was refluxed for 24 hours and was then cooled. The mixture was vacuum filtered to obtain 21 g of 4-chloroformyl-4-thiazoline-2-one melting at 184°C.

A mixture of 10 g of 4-chloroformyl-4-thiazoline-2-one and 100 ml of 2-butanol was refluxed for 6 hours and excess alcohol was evaporated. The residue was crystallized from isopropyl ether to obtain 6 g of 4-(2'-butoxycarbonyl)-4-thiazoline-2-one melting at 50°C.

A mixture of 6.3 g of 4-(2'-butoxycarbonyl)-4-thiazoline-2-one, 75 ml of acetone and 5.52 g of potassium carbonate was refluxed for 1½ hours and then 5.64 g of 0,0-diethyl chlorothiophosphate were added. The mixture was stirred for 18 hours at room temperature and was filtered. The filtrate was concentrated to dryness and the residue was chromatographed over silica gel. Elution with an 8-2 cyclohexane-ethylacetate mixture yielded 8 g of 2-diethoxythiophosphoryloxy-4-(2'-butoxycarbonyl)-thiazole with a refractive index of $n_D^{19} = 1.509$ Analysis: $C_{12}H_{20}NO_5PS_2$ Calculated: %C 40.79, %H 5.71, %N 3.97, %P 8.77; Found: %C 41.3, %H 5.8, %N 4.0, %P 8.6.

INSECTICIDAL ACTIVITY

The insecticidal activity was determined with 4-ethoxycarbonyl-2-(diethoxythiophosphoryloxy)-thiazole [Compound A] and 4-ethoxycarbonylmethyl-2-(diethoxythiophosphoryloxy)-thiazole [Compound B].

A. Insecticidal activity against Mamestra brassicae caterpillars

This test was effected on Mamestra brassicae caterpillars in the last larvae stage with a body of 1.5 to 2.0 cm. 1 μl of an acetone solution of the test compound was applied topically to the dorsal thorax of each caterpillar using 10 caterpillars for each dose studied and the caterpillars were kept at 25°C. The number of dead and living caterpillars was determined 24 and 48 hours after the topical application and the percentage of mortality was determined for compound A. At a dose of 10 μg of compound A per caterpillar, the percent of mortality was 100% after 24 and 48 hours which means the product had a good insecticidal activity in this test.

B. Insecticidal activity against Mamestra oleracea caterpillars

Test A was repeated using Mamestra oleracea caterpillars and the results with compound A are reported in Table I.

TABLE I

| μg of compound A | % mortality after 24 hr. | 48 hr. |
|---|---|---|
| 10 | 100 | 100 |
| 1 | 40.0 | 50.0 |

Compound A has good insecticidal activity against Mamestra oleracea caterpillars.

C. Spodoptera exigua and Chilo suppressalis caterpillars

The procedure of Test A was repeated with Spodoptera expigua and Chilo suppressalis caterpillars with compound A and the results are reported in Table II.

TABLE II

| Caterpillar | Dose in μg | % Mortality after 24 hr. | 48 hr |
|---|---|---|---|
| Spodoptera exigua | 10 | 100 | 100 |
|  | 1 | 90.0 | 90.0 |
| Chilo suppressalis | 10 | 100 | 100 |
|  | 1 | 100 | 100 |

Table II shows that compound A has good insecticidal activity against these caterpillars.

D. Sitophilus granarius 0.2 μl of an acetone solution of the test product was applied to the ventral thorax of each insect at concentrations of 5000 and 500 ppm with 50 insects for each test. The insects were held at 20°C and the percent of mortality was determined 24 and 48 hours and 6 days after the treatment. The results with compound A are reported in Table III.

TABLE III

| Dose in μg | % mortality after 24 hr. | 48 hr. | 6 days |
|---|---|---|---|
| 1000 | 100 | 100 | 100 |

TABLE III-continued

| Dose in μg | 24 hr. | % mortality after 48 hr. | 6 days |
|---|---|---|---|
| 100 | 6.0 | 6.0 | 10.0 |

The results of Table III show the good insecticidal activity of the product in this test:

E. Drosophila melanogaster 2 ml of an acetone solution of the test product at concentrations of 5000, 500 and 50 ppm were placed in the bottom of a crystallizer and were then allowed to dry for 1 hour under a laboratory atmosphere. Three tests were run for each concentration and 25 to 50 drosophiles were placed in the crystallizer together with a carrot ring which acted as nutrient for the insects. The crystallizers were closed with a Petri dish cover and they were stored at 20°C. The number of living and dead insects was determined after 1,2,4 and 24 hours and the results for compound A are reported in Table IV.

TABLE IV

| Mg of compound A/liter | % Efficacy after hours | | | |
|---|---|---|---|---|
| | 1 | 2 | 4 | 24 |
| 5000 | 0 | 0 | 5.9 | 100 |
| 500 | 0 | 0 | 0 | 100 |
| 50 | 0 | 0 | 0 | 32.80 |

Table IV shows that compound A has good contact and vapor insecticidal activity against Drosophila melanogaster.

F. Ceratitis capitata

This test was effected topically with acetone solutions of 1000 or 100 mg of compound A per liter and 1 μl of the solution was applied to the dorsal thorax of Ceratitis capitata flies aged 25 days (± 0.5) using 50 insects for each concentration. The number of flies still living and dead was determined after 2 and 24 hours to determine the percent of mortality. The results are reported in Table V and they show compound A to have a good insecticidal activity against Ceratitis capitata.

TABLE V

| mg of compound A | % Mortality after hours | |
|---|---|---|
| | 2 | 24 |
| 1000 | 91.7 | 97.9 |
| 100 | 61.2 | 38.8 |

G. Blatella germanica

1 μl of an acetone solution of the test product was applied to the ventral thorax of the insects with 20 insects per dose and concentrations of 2500, 1250, 625 and 312,5 mg/liter. The number of living and dead insects 24 and 48 hours and 6 days after the treatment was determined and the results were reported in Table VI.

TABLE VI

| Compound | mg/liter | 24 hr. | % mortality after 48 hr. | 6 days |
|---|---|---|---|---|
| A | 2500 | 95.0 | 95.0 | 100 |
| | 1250 | 90.0 | 95.0 | 100 |
| | 625 | 10.0 | 10.0 | 15.0 |
| B | 1250 | 100 | 100 | 100 |
| | 625 | 100 | 100 | 100 |
| | 312,5 | 90 | 90 | 90 |

Table VI shows that compounds A and B have good insecticidal activity against Blatella germanica.

NEMATOCIDAL ACTIVITY

A. Panagrellus silusae

About 2000 nematodes suspended in 0.5 ml of water were placed in a container of about 50 ml and 10 ml of an aqueous suspension of the test compound at a concentration of 1 or 0.1 g/liter were added thereto using 3 tests for each concentration. After homogenization of the aqueous media for 24 hours, a 1 ml sample was taken and the living and dead nematodes were counted with a Peter sheet. The results are reported in Table VII.

TABLE VII

| Compound | Dose in g/l | % mortality |
|---|---|---|
| A | 1 | 100 |
| | 0.1 | 86.5 |
| B | 1 | 100 |
| | 0.1 | 100 |

B. Ditylenchus myceliophagus

Test A was repeated with Ditylenchus myceliophagus and the results are reported in Table VIII.

TABLE VIII

| Compound | Dose in g/l | % mortality |
|---|---|---|
| A | 1.0 | 100 |
| | 0.1 | 88.4 |
| B | 1.0 | 100 |
| | 0.1 | 55.7 |

Tables VII and VIII shows that compounds A and B possess good nematocidal activity against the test species.

ACARICIDAL ACTIVITY

A. Ovicide Activity

Bean leaves infested with 10 Tetranychus urticae females per leaf and coated with glue about their periphery were used in this test and the females were left to lay eggs for 24 hours and were then removed from the leaves which were egg infested and divided into 2 groups. The first group was sprayed with 0.5 ml of an aqueous solution of compound A for each leaf at concentrations of 50 or 10 mg per liter and the second group was untreated to act as controls. The number of living eggs 9 days after the treatment was determined and the percent of egg mortality was determined and reported in Table IX.

TABLE IX

| Product | Concentration in mg/liter | % Mortality |
|---------|---------------------------|-------------|
| A       | 50                        | 100         |
|         | 10                        | 93.3        |
| Controls| 0                         | 6.8         |

B. Adulticide Test

Bean leaves infested with 25 acarids per leaf and coated with glue about their edge were divided into 2 groups. The first group was sprayed with 2.5 ml of an aqueous solution of the test compound A for each leaf at concentrations of 50, 10 and 1 mg/liter. The second control group was untreated and the number of acarids living 48 hours after the spraying was determined to determine the percent of mortality. The results are reported in Table X.

TABLE X

| Product | Concentration in mg/liter | % Mortality |
|---------|---------------------------|-------------|
| A       | 50                        | 100         |
|         | 10                        | 100         |
| B       | 50                        | 100         |
|         | 10                        | 96          |
|         | 1                         | 20          |
| Controls| 0                         | 4           |

C. Larvicide Test

This test was similar to the ovicide test but the readings were effected 9 days after the treatment to allow time for the insects to evolve. The reslts are reported in Table XI.

TABLE XI

| Product | Concentration in mg/liter | % Mortality |
|---------|---------------------------|-------------|
| A       | 50                        | 100         |
|         | 10                        | 100         |
| Controls| 0                         | 9.8         |

These tests show that the products tested have a good acaricide activity against Tetranychus urticae.

Various modifications of the products and processes of the invention may be made without departing from the spirit or scope thereof and it is to be understood that the invention is to be limited only as defined in the appended claims.

We claim:

1. A compound of the formula

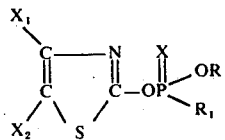

wherein X is selected from the group consisting of oxygen and sulfur, $X_1$ is selected from the group consisting of alkyl of 1 to 6 carbon atoms, cyano and

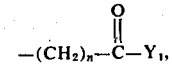

$Y_1$ is selected from the group consisting of alkyl of 1 to 6 carbon atoms, alkoxy of 1 to 6 carbon atoms and amino, $n$ is 0, 1 or 2, $X_2$ is selected from the group consisting of hydrogen, chlorine, bromine, alkyl of 1 to 6 carbon atoms, cyano and

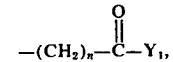

R is alkyl of 1 to 6 carbon atoms, $R_1$ is selected from the group consisting of alkyl of 1 to 6 carbon atoms, alkoxy of 1 to 6 carbon atoms and

and $R_2$ and $R_3$ are selected from the group consisting of hydrogen and alkyl of 1 to 6 carbon atoms with the proviso that $X_1$ is other than alkyl when $X_2$ is alkyl or hydrogen.

2. The compound of claim 1 wherein $R_1$ is selected from the group consisting of alkyl and alkoxy of 1 to 6 carbon atoms.

3. A compound of claim 1 wherein X is sulfur, $X_1$ is selected from the group consisting of alkyl of 1 to 6 carbon atoms, cyano and

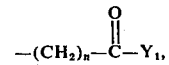

$Y_1$ is selected from the group consisting of amino and alkyl and alkoxy of 1 to 3 carbon atoms, $n$ is 0, 1 or 2, $X_2$ is selected from the group consisting of hydrogen, chlorine, bromine, alkyl of 1 to 6 carbon atoms, cyano and

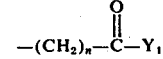

and $R_1$ is selected from the group consisting of methyl, methylamino and alkoxy of 1 to 3 carbon atoms.

4. The compound of claim 1 which is 4-ethoxycarbonyl-2-(diethoxythiophosphoryloxy)-thiazole.

5. The compound of claim 1 which is 4-ethoxycarbonylmethyl-2-(diethoxythiophosphoryloxy)-thiazole.

6. The compound of claim 1 which is 5-acetyl-2-(diethoxythiophosphoryloxy)-4-methyl-thiazole.

7. The compound of claim 1 which is 5-ethoxycarbonyl-2-(diethoxythiophosphoryloxy)-4-methyl-thiazole.

8. The compound of claim 1 which is 5-methoxycarbonyl-4-methoxycarbonylmethyl-2-(diethoxythiophosphoryloxy)-thiazole.

9. The compound of claim 1 which is 5-ethoxycarbonyl-methyl-2-(diethoxythiophosphoryloxy)-4-methyl-thiazole.

10. The compound of claim 1 which is 5-cyano-2-(diethoxythiophosphoryloxy)-4-methyl-thiazole.

11. The compound of claim 1 which is 5-bromo-4-ethoxycarbonyl-2-(diethoxythiophosphoryloxy)-thiazole.

12. The compound of claim 1 which is 4,5-diethoxycarbonyl-2-(diethoxythiophosphoryloxy)-thiazole.

13. The compound of claim 1 which is 4-ethoxycarbonyl-2-(diethoxythiophosphoryloxy)-5-n-hexyl-thiazole.

14. The compound of claim 1 which is 4-ethoxycarbonyl-2-(diethoxythiophosphoryloxy)-5-ethoxycarbonyl-methyl-thiazole.

15. The compound of claim 1 which is 4-methoxycarbonyl-2-(diethoxythiophosphoryloxy)-thiazole.

16. The compound of claim 1 which is 4-isopropoxycarbonyl-2-(diethoxythiophosphoryloxy)-thiazole.

17. The compound of claim 1 which is 4-acetyl-2-(diethoxythiophosphoryloxy)-thiazole.

18. The compound of claim 1 which is 4-carbamoyl-2-(diethoxythiophosphoryloxy)-thiazole.

19. The compound of claim 1 which is 4,5-di-ethoxycarbonylmethyl-2-(diethoxythiophosphoryloxy)-thiazole.

20. The compound of claim 1 which is 5-ethoxycarbonyl-4-[(2'-ethoxycarbonyl)-ethyl]-2-(diethoxythiophosphoryloxy)-thiazole.

21. The compound of claim 1 which is N-methyl-thiophosphoramidate of O-ethyl and of O-[2-(4-ethoxycarbonylthiazolyle)].

22. The compound of claim 1 which is methylthiophosphonate of O-ethyl and of O-[2-(4-ethoxycarbonylthiazolyle)].

23. The compound of claim 1 which is 4-cyano-2-(diethoxythiophosphoryloxy)-thiazole.

* * * * *